(12) United States Patent
Honeycutt et al.

(10) Patent No.: US 9,020,590 B1
(45) Date of Patent: Apr. 28, 2015

(54) APPARATUS TO TRANSCUTANEOUSLY STIMULATE RESONANT FREQUENCIES OF MAMMALS

(76) Inventors: James David Honeycutt, Vancouver, WA (US); Vickie Lynn Honeycutt, Vancouver, WA (US)

( * ) Notice: Subject to any disclaimer, the term of this patent is extended or adjusted under 35 U.S.C. 154(b) by 998 days.

(21) Appl. No.: 13/015,178

(22) Filed: Jan. 27, 2011

Related U.S. Application Data

(60) Provisional application No. 61/298,838, filed on Jan. 27, 2010.

(51) Int. Cl.
| | | |
|---|---|---|
| A61M 21/02 | (2006.01) | |
| A61N 5/06 | (2006.01) | |
| A61N 2/02 | (2006.01) | |
| A61N 1/36 | (2006.01) | |

(52) U.S. Cl.
CPC ............... *A61N 2/02* (2013.01); *A61N 5/0618* (2013.01); *A61N 1/36171* (2013.01)

(58) Field of Classification Search
CPC ........... A61N 1/025; A61N 1/32; A61N 1/36; A61N 1/36014
USPC .................................... 607/50, 68–74; 600/14
See application file for complete search history.

(56) References Cited

U.S. PATENT DOCUMENTS

| | | | |
|---|---|---|---|
| 5,048,523 A | | 9/1991 | Yamasawa |
| 5,183,041 A | | 2/1993 | Toriu |
| 5,441,528 A | * | 8/1995 | Chang et al. ................ 607/69 |
| 5,725,560 A | | 3/1998 | Brink |
| 5,817,138 A | * | 10/1998 | Suzuki ........................... 607/67 |
| 6,023,642 A | | 2/2000 | Shealy |
| 6,051,959 A | * | 4/2000 | Tupper ........................... 322/78 |
| 6,076,018 A | | 6/2000 | Sturman |
| 6,161,044 A | | 12/2000 | Silverstone |
| 6,447,499 B2 | * | 9/2002 | Gray ............................. 604/500 |
| 6,526,319 B2 | * | 2/2003 | Kobayashi ..................... 607/72 |
| 7,200,434 B2 | | 4/2007 | Havel |
| 8,167,784 B1 | * | 5/2012 | Honeycutt et al. ............. 600/14 |
| 2006/0206174 A1 | * | 9/2006 | Honeycutt et al. ............. 607/88 |

OTHER PUBLICATIONS

U.S. Appl. No. 12/345,124, filed Aug. 27, 2009, Ewing.
U.S. Appl. No. 11/927,597, filed Mar. 27, 2008, Harry.
U.S. Appl. No. 11/307,348, filed Sep. 14, 2006, Honeycutt.
U.S. Appl. No. 11/949,717, Honeycutt.
U.S. Appl. No. 11/518,614, filed Nov. 8, 2007, Winey.

\* cited by examiner

*Primary Examiner* — Carl H Layno
*Assistant Examiner* — Jon Eric C Morales

(57) ABSTRACT

An apparatus to stimulate resonant frequencies of mammals, including humans, through transcutaneously applied bipolar micro-current therapeutic frequencies eXclusive OR (XOR) modulated over a variable duty cycle carrier square wave. A Fibonacci number clocked stored-program microcontroller generates a variable duty cycle higher frequency pulse width modulation (PWM) carrier square wave output which is XOR modulated with a lower therapeutic frequency square wave output to control an H-Bridge driver capacitive coupled to an isolation transformer. The preferred embodiment supports one or more user inputs and displaying program and operational information on a suitable display. Further, using an H-Bridge to drive an inductive load with bi-polar pulses creates scalar waves when the H-Bridge's output is switched from one polarity to the opposite each time the therapeutic low frequency square wave output XOR modulates the higher frequency PWM square wave.

11 Claims, 6 Drawing Sheets

Figure 1a. Prior Art – Mono-Polar Pulse Driver
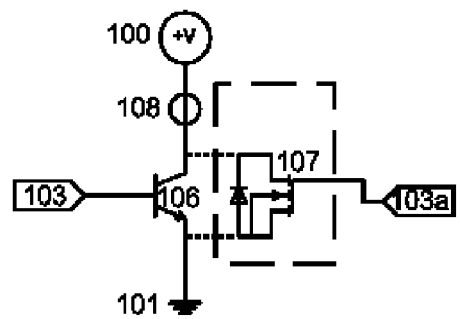
Figure 1b. Prior Art Waveforms – Mono-Polar Pulse
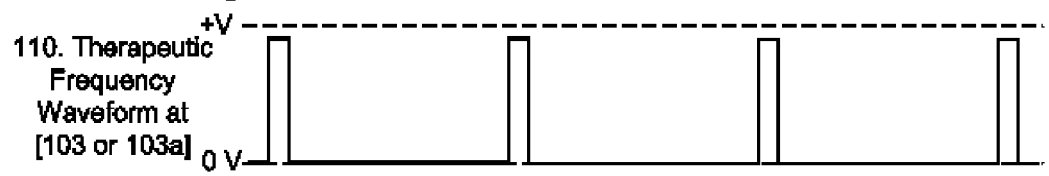
110. Therapeutic Frequency Waveform at [103 or 103a]
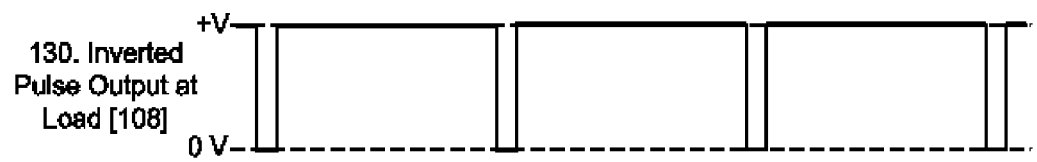
130. Inverted Pulse Output at Load [108]
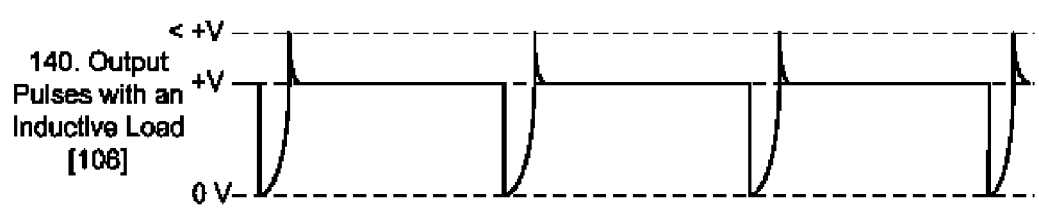
140. Output Pulses with an Inductive Load [108]

Figure 2a. Prior Art – Mono-Polar AND Modulated PWM Pulse Driver
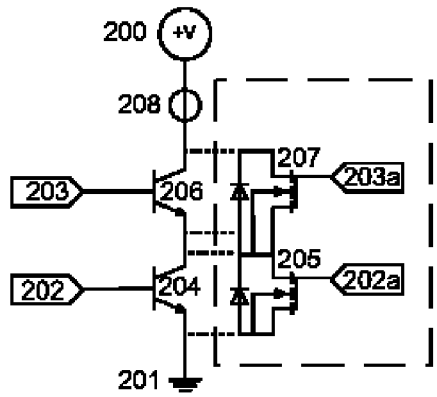
Figure 2b. Prior Art Waveforms – Mono-Polar AND Modulated PWM Pulses
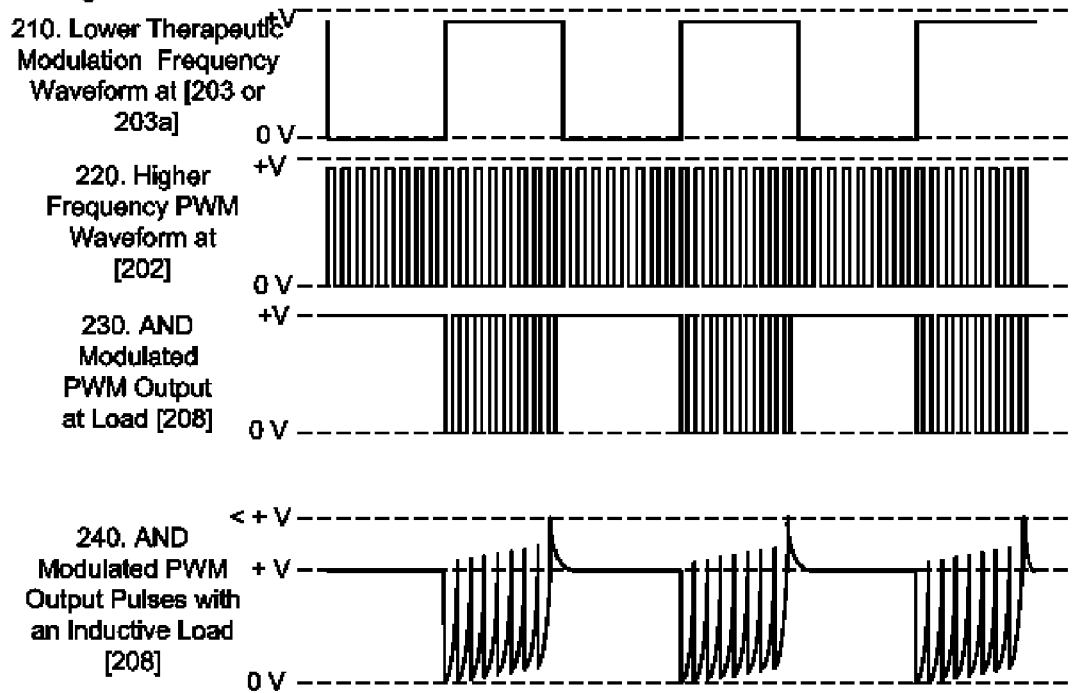

Figure 3a. Prior Art – Mono-Polar AND Modulated PWM Pulse Driver
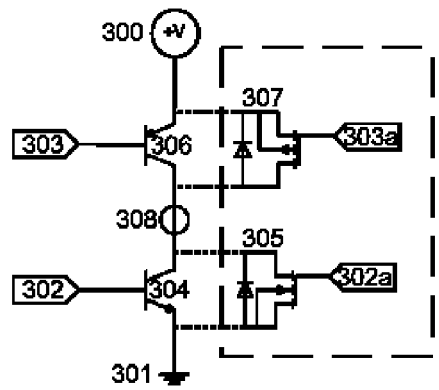
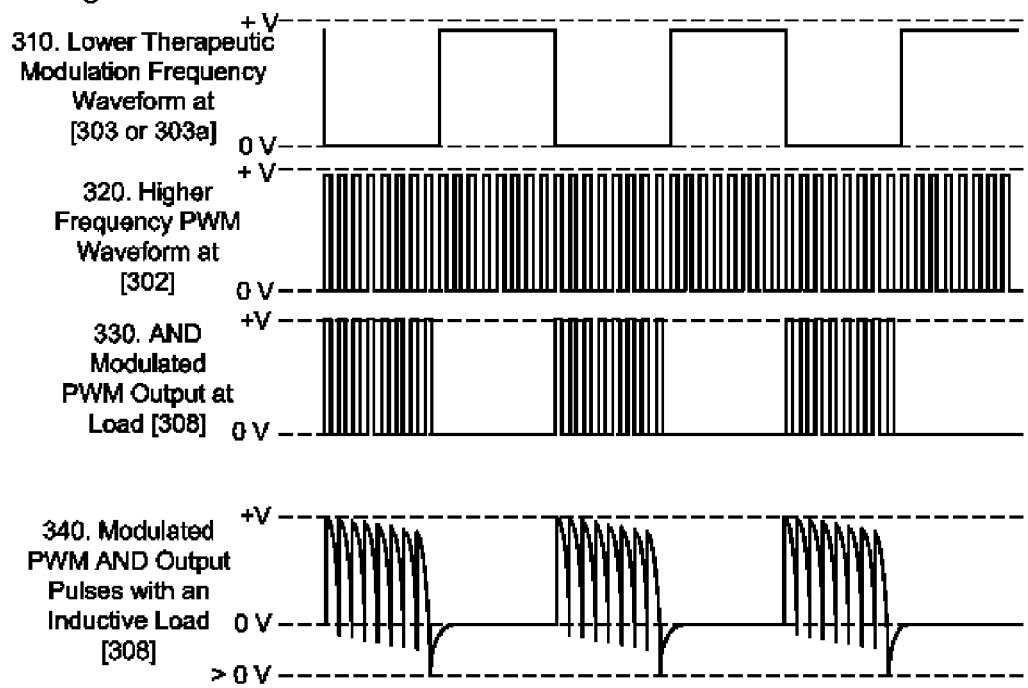

Figure 4a. New Apparatus - Bipolar XOR Modulated PWM Using H-Bridge

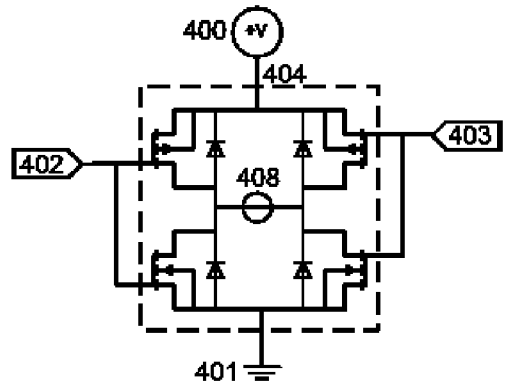

Figure 4b. New Apparatus Waveforms - Bipolar XOR Modulated PWM Using H-Bridge, showing scalar components as arrows

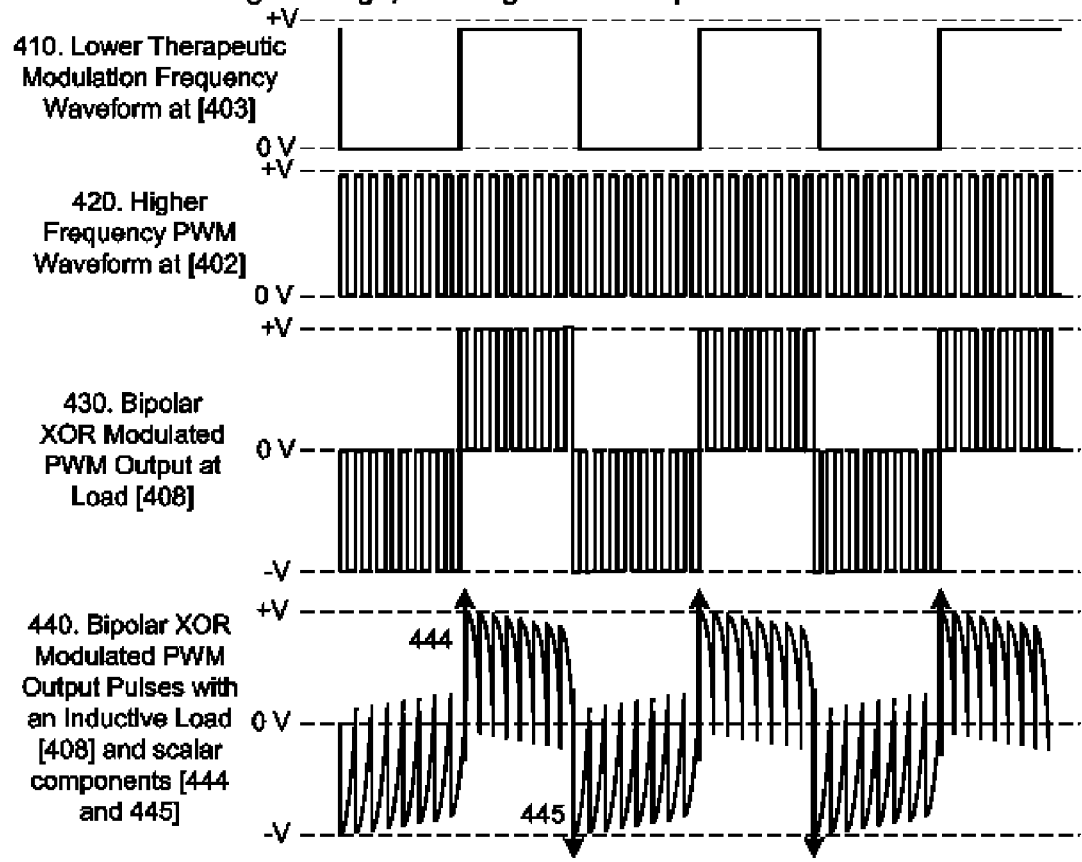

410. Lower Therapeutic Modulation Frequency Waveform at [403]

420. Higher Frequency PWM Waveform at [402]

430. Bipolar XOR Modulated PWM Output at Load [408]

440. Bipolar XOR Modulated PWM Output Pulses with an Inductive Load [408] and scalar components [444 and 445]

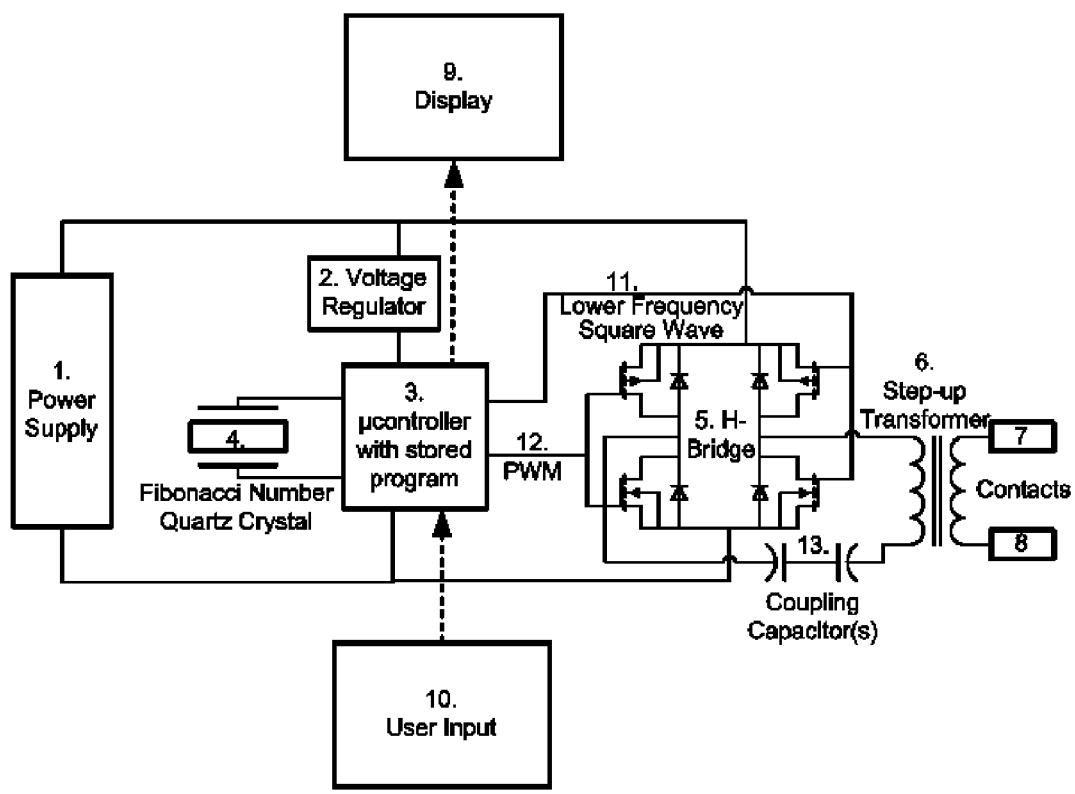

Software Flowchart

APPARATUS TO TRANSCUTANEOUSLY STIMULATE RESONANT FREQUENCIES OF MAMMALS

CROSS-REFERENCE TO RELATED APPLICATION

This application claims the benefit of U.S. Provisional Application No. 61/298,838, filed Jan. 27, 2010. The foregoing application is herein incorporated by reference in its entirety.

FIELD OF THE INVENTION

This invention relates to transcutaneously applied microcurrents of two or more eXclusive-OR (XOR) mixed resonant frequencies for therapeutic purposes. The therapeutic application of resonant frequencies may be applied, but is not limited to, massage therapy and bodywork, acupuncture and acupressure, Functional Electrical Stimulation (FES) for Spinal Cord Injuries (SCI) and Central Nervous System (CNS) damage from strokes or external trauma, muscle strain and related injuries and post-operative joint replacement and related surgeries.

BACKGROUND OF THE INVENTION

Over 200 years ago the Italian Galvani discovered electrical current caused muscle cells to contract. Since then electrical currents have been applied in numerous therapeutic applications and methods, and when applied to muscles they have been used to cause similar contractions. This use of electricity has been expanded to support adaptive neuroplasticity for spinal cord injury (SCI) and Central Nervous System (CNS) affected patients, such as stroke survivors. The most prevalent forms of this electrical stimulation are Transcutaneous Electrical Nerve Stimulators (TENS), which operate using short pulse durations designed to cause rapid muscle contractions, and Functional Electrical Stimulation (FES) which uses longer electrical pulse durations for SCI and CNS stimulation.

It is well known in the art that all organisms are energy systems comprised of interrelated organized atoms bound together by molecular electromagnetic forces. These atoms all have unique resonant frequencies caused by the rotation of electrons around a positively charged nucleus. Likewise, every molecule, cell and organ within any organism, including all mammals, has its own resonant frequency. However, the resonant frequencies of those cells and organs can change and become out-of-balance as a result of injury, abuse or illness. Stimulating out-of-balance cells and organs with externally applied resonant frequencies can reveal such instances of injury, abuse or illness. For example, Magnetic Resonance Imaging (MRI) relies upon the principle of atomic resonance in order to stimulate the targeted atoms within its imaging field to absorb and then release a burst of radio frequency energy tuned to the specific resonant frequency of the specific type of atom, usually hydrogen, within a given strength of a static magnetic field, thus supporting the concept of resonances in the organic systems. What is desired is a way to aid the damaged tissues in their natural recovery by manipulation of their natural resonant frequencies. The most common forms of this manipulation, TENS and FES, however, do not affect the resonant frequencies of the damaged tissue. Instead TENS treatments use short electrical pulses specifically to create muscle contractions, and FES uses a longer pulse duration to specifically aid SCI and CNS patients.

Apparatuses for TENS treatment could possibly be used to affect the resonant frequencies of damaged tissue, but those designed to date have several qualities making such use unlikely and undesirable. First, the particular pulse frequency used must be based on natural healing frequencies, known in the art as Rife frequencies. Second, the electrical pulses should be bipolar, rather than monopolar, such that standing scalar waves are created. Third, the pulses of TENS devices are sufficiently strong to cause muscle contraction, an undesirable effect to achieve resonant frequency stimulation. Finally, there should be mixing of high and low frequency signals to allow for shorter duty cycles coupled with increased energy efficiency.

BRIEF SUMMARY OF THE INVENTION

The invention disclosed and claimed herein addresses the above and other needs and provides means and systems for stimulating the resonant frequencies of organisms using an apparatus to generate precise frequency stimulation, which is bipolar and has an effective energy of one to two orders of magnitude below that of traditional TENS units.

According to the present invention, stimulation of the resonant frequencies of organisms occurs using an apparatus to generate precise frequency stimulation. These precise frequencies are achievable by the XOR modulation of a higher Pulse Width Modulation (PWM) frequency with a desired lower therapeutic frequency using either a full or half H-Bridge MOSFET driver as shown in FIG. 4a. Whereas the prior art's use of a logical AND function to modulate a carrier PWM signal created a monopolar signal, the present invention XOR modulates the higher frequency PWM signal to create a unique bipolar waveform 430 shown in FIG. 4b.

In addition to creating the unique waveform 430, the use of either a full or half H-Bridge to drive an inductive load, according to the present invention, causes the creation of standing electromagnetic waves, also known as scalar waves, to be emitted from the inductor upon each XOR modulation of the lower therapeutic frequency as shown by the waveform 440. When the bi-polar output of the apparatus is switched due to a change in the lower modulating therapeutic frequency, this current reversal causes a collision with the stored current in the inductor and this collision in turn creates a scalar wave component. These scalar waves are created both within Transformer 6, shown in FIG. 5, and within the body of the connected mammal, as the body of a mammal presents an inductive load to the output of Transformer 6 through electrical Contacts 7 and 8.

The possible therapeutic frequencies are stored and executed within a microcontroller. This microcontroller supports the independent generation of a PWM square wave with a duty cycle that can be changed while the program is running, and thereby supports the ability to maintain a constant duty cycle with each transition of the therapeutic frequency. The duty cycle changes also support the adjustment of the effective power level of the frequency stimulation presented to the mammal.

BRIEF DESCRIPTION OF THE DRAWINGS

FIGS. 1a and 1b show the typical prior art and resulting waveforms

FIGS. 2a and 2b show the prior art with a PWM signal added

FIGS. 3a and 3b show the prior art with load moved between the two driving elements FIGS. 4a and 4b show the XOR arrangement of the present invention FIG. 5 is schematic representation of the preferred embodiment

DETAILED DESCRIPTION

Figure 6:
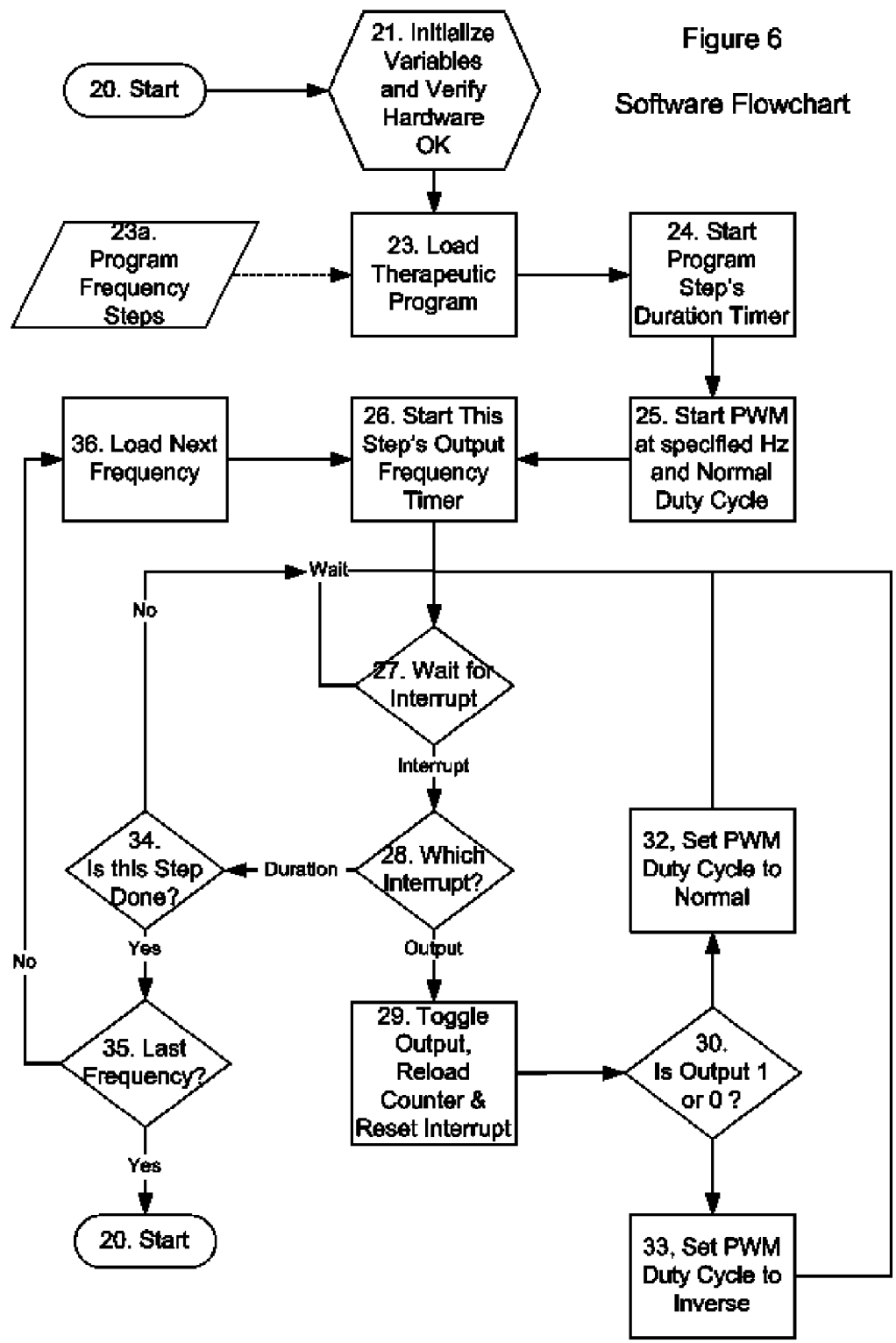
FIG. 6 is the software flowchart for the embodiment's microcontroller

FIG. 1a presents the basic prior art used in the output stage to generate an electrical pulse to cause muscle contractions in TENS types of devices and for frequency stimulus generators that use square wave pulses to drive an inductor or similar electromagnetic coil used to generate electromagnetic flux or for those that generate high voltage E-Fields. The prior art in FIG. 1a consists of some positive voltage (+V) 100 and a ground potential 101, input 103 from the signal generator which biases NPN Transistor 106. Alternatively, N-Channel MOSFET 107 may be used as driven by input 103a. When a positive signal 110 is applied at 103 or 103a, Transistor 106, or MOSFET 107 respectively, will conduct current and thus supply a ground potential across load 108 which is connected to +V 100. FIG. 1b shows the relevant signal 110 used to operate the prior art in FIG. 1a and resultant output waveform 130 when driving a resistive load 108 and waveform 140 when driving an inductive load 108.

FIG. 2a represents prior art similar to FIG. 1a with an additional Pulse Width Modulation (PWM) input 202 or 202a used to bias an additional NPN Transistor 204 or N-Channel MOSFET 205 which is connected in a logical AND configuration with Transistor 206 or MOSFET 207 respectively. The additional Transistor 206 or MOSFET 207 forms a logical AND gate function with its respective series connected transistor 204 or MOSFET 205, such that when desired therapeutic modulation frequency input signal 210 is applied to input 203 or 203a is high, AND high frequency PWM input signal 220 is applied to 202 or 202a is also high, a Boolean one or True exists, then the load 208 will be connected across both +V 200 and Ground potential 201. FIG. 2b shows the relevant lower therapeutic modulation frequency waveform 210 driving input signal 203 or 203a, and the higher frequency PWM waveform 220 driving input signal 202 or 202a. The use of a PWM signal is generally designed to vary the duty cycle of the resultant pulsed waveform 230 that is used to pulse Load 208. Waveform 240 shows the results if an inductive Load 208 is driven instead of a purely resistive load as shown in waveform 230.

FIG. 3a shows a typical variation of FIG. 2a where Load 308 is connected between a PNP Transistor 306 or P-Channel MOSFET 307 to supply +V 300 and an NPN Transistor 304 or N-Channel MOSFET 305 to supply the ground potential 301. When the lower therapeutic modulation frequency signal 310 at input 303 or 303a is low and the higher frequency PWM signal 320 input at 302 or 302a is high then both series connected transistors or MOSFETs conduct the current to power Load 308. This is still a logical AND function, but with an inverted input on desired therapeutic modulation frequency input 303 or 303a. FIG. 3b shows the relevant lower therapeutic modulation frequency waveform 310 driving input signal 303 or 303a and higher frequency PWM waveform 320 driving input signal 302 or 302a. Waveform 330 shows the resulting PWM AND modulated output driving a purely resistive load 308 and waveform 340 shows the resulting PWM AND modulated output driving an inductive load 308.

FIG. 4a shows the output portion of the present invention in contrast to the Prior Art in FIGS. 1a through 3b inclusive to illustrate the use of the XOR modulation of the two square waves to achieve the unique wave forms and scalar components. H-Bridge 404 is shown in a half H-Bridge connection scheme such that the gate inputs of the N-Channel MOSFET and P-Channel MOSFET on the left side are connected together and form high frequency PWM input 402, as are the gate inputs of N-Channel MOSFET and P-Channel MOSFET on the right side connected together and form lower therapeutic frequency input 403. This is sometimes called a half H-Bridge configuration and is used in the preferred embodiment as it reduces the number of controlling lines needed on the microcontroller. A full H-Bridge is also covered by the present invention. When 402 and 403 are both high, logical ones, their respective P-Channel MOSFETs are turned off and their respective N-Channel MOSFETs are turned on and as a result a ground potential 401 is presented to both sides of load 408 and no current is conducted. The inverse is true when 402 and 403 are both low, logical zeroes, +V 400 is presented to both sides of load 408 and no current is conducted. Only when inputs 402 and 403 are opposite (XOR) of each other, does the logical one side of the H-Bridge conducts its side of load 408 to +V 400 and the logical zero side of the H-Bridge conducts its side of load 408 to ground 401. Thus the H-Bridge only conducts current across load 408 when the inputs 402 and 403 are valid for an XOR logical function.

The driving inputs and resultant outputs waveforms are shown in FIG. 4b. Signal 410 is the lower therapeutic frequency. Signal 420 is the higher PWM frequency whose duty cycle is varied under programmatic control, and is XOR'd with signal 410 to create the resulting bipolar output signal 430 and 440. Waveform 440 includes scalar components 444 and 445, which occur when an inductive load is driven and signal 410 switches its input polarity causing a reversal in the stored energy in the driven inductor.

FIG. 5 presents the preferred embodiment of the present invention. In the present invention Microcontroller 3 is capable of generating a variable duty cycle higher frequency pulse width modulation (PWM) square wave 12 which is XOR modulated with the lower therapeutic frequency square wave 11 using a half H-Bridge 5 which consists of 2 N-Channel semiconductors and 2 P-Channel semiconductors arranged so that the current across a connected Load 6 can be switched in polarity. Alternatively a full H-Bridge can be used requiring four controlling outputs from Microcontroller 3. All frequencies are derived from a quartz crystal timing element 4 with a fundamental frequency which deviates less than 1% from a Fibonacci number. In the preferred embodiment the crystal frequency selected is 24,000,000 Hz which is 0.66% from the Fibonacci number 24,157,817.

The higher frequency PWM square wave 12 in the preferred embodiment is selected to be 20,000 Hz. The PWM frequency can be a higher or lower frequency and should be at least 4 times higher than the highest desired therapeutic frequency and no higher than the rated bandwidth of step-up isolation Transformer 6. Transformer 6 is used to both increase the driving voltage from the apparatus' power supply 1 to a sufficient level to overcome the galvanic resistance of mammalian skin when attached through electrical Contacts 7 and 8, and to provide isolation between the apparatus and the subject connected to contacts 7 and 8. An audio band step-up transformer is used in the preferred embodiment as the bandwidth frequency of most power transformers is 50 to 60 Hz, which is inefficient for higher PWM frequencies, resulting in poor coupling and excessive heat generation in the windings of the transformer. The output of H-Bridge 5 is capacitive coupled through two polarized Capacitors 13 connected with either their positive or negative ends together to the input of the audio band step-up Transformer 6 to reduce the DC resistance load on H-Bridge 5 and to reduce the DC current carried by Transformer 6. Alternatively a non-polarized capacitor 13 could be used. Suitable electrical contacts 7 and 8 are used to make transcutaneous connection with the skin of the mammal. Voltage Regulator 2 conditions the voltage from power supply 1, which may be a battery or other suitable power supply source, to be appropriate for operating microcontroller 3. Microcontroller 3 contains a stored program for the both the operating software as well as the programmatic frequencies used. Display 9 provides status and operational information to the user and may be any combination of indicators and/or information displays as required. User input 10 may be any combination of switches, potentiometers, touch sensors, or other typical human input devices used to control the operation of the apparatus.

FIG. 6 presents a flow chart of the stored program in Microcontroller 3 of FIG. 5. The process flow begins at the Start step 20. Initialization 21 verifies the hardware is functional and preset all program variables to their appropriate idle state. At step 23 Microcontroller 3 loads the desired therapeutic program 23a that contains one or more steps and each step contains the frequency and duration for that step. In step 24 the first therapeutic program step is loaded and its duration timer is started. At step 25 the PWM frequency is started at the desired duty cycle and the step's frequency timer is started at step 26 when a logical '1' is output on the modulated frequency output line. At step 27 microcontroller 3 waits for an interrupt to occur and at step 28 determines the interrupt type. If it is the step duration the program branches to step 34 to determine if the step is completed and if so the program branches to step 35 to determine if this was the last step. If this was the last step then the program restarts at 20. If it is not the last step then the program branches to step 36 and the next step is loaded and control continues at step 26 to repeat. If at step 28 the interrupt was a modulation frequency interrupt the program branches to step 29 where the interrupt is restarted and the modulation output is toggled from either a '1' to a '0' or from a '0' to a '1' using a logical XOR function on that specific port pin of the microprocessor. Control passes to step 30 where If the modulated output went to a '0' then control is passed to step 33 and the PWM duty cycle is inverted to maintain the same duty cycle with the inverted modulated output. If the modulated output went to a '1' then control is passed to step 32 and the PWM duty cycle is returned to its normal setting. In either case, control is passed to step 27 where it waits for the next interrupt.

| Definition List 1 | |
|---|---|
| Term | Definition |
| CNS | Central Nervous System |
| DC | Direct Current |
| Hz | Hertz - Cycles Per Second |
| PWM | Pulse Width Modulation |
| MOSFET | Metal Oxide Substrate Field Effect Transistor |
| MRI | Magnetic Resonance Imaging |
| SCI | Spinal Cord Injury |
| TENS | Transcutaneous Electrical Nerve Stimulator |
| XOR | eXclusive OR logical function |

What is claimed is:

1. An apparatus for frequency stimulation of a mammal's tissues configured for applying micro-currents directly to skin of a mammal, the apparatus comprising:
   a power supply,
   a microcontroller,
   a quartz crystal for clocking said microcontroller,
   a storage device storing one or more programs, said programs being timed sequences of Rife frequencies, and
   the storage device further storing instructions for controlling the microcontroller to perform steps comprising:
      producing a first square wave signal having a frequency based at least in part upon a fundamental frequency of the quartz crystal and a Rife frequency in said one or more stored programs;
      producing a second square wave signal having a frequency based at least in part upon a fundamental frequency of the quartz crystal with a variable duty cycle wherein the second square wave signal's frequency is at least four times greater than the first square wave signal's frequency;
      alternating the variable duty cycle of the second square wave signal in step with the first square wave signal;
   an H-bridge acting as an eXclusive OR (XOR) to modulate the first and second square wave signals to produce a mixed bi-polar square wave signal with a voltage based at least in part upon the power supply and the XOR modulation of the first and second square wave signals,
   a step-up transformer capacitively coupled to the H-bridge to increase the voltage of the mixed bi-polar square wave signal to overcome the skin resistance of a mammal's tissues, and
   electrical contacts to apply the voltage increased mixed bi-polar square wave signal directly to a mammal's tissues.

2. The apparatus of claim 1, wherein the quartz crystal has a fundamental frequency which is less than 1% from a Fibonacci number in an inclusive range of 75,000 Hz to 102,000,000 Hz.

3. The apparatus of claim 1, wherein the variable duty cycle of the second square signal is varied such that the micro-currents of the voltage increased mixed bipolar square wave signal applied by the electrical contacts directly to a mammal's tissues have a current in an inclusive range of 0.1 milliamperes to 100 milliamperes being sufficiently low enough to not cause muscle tissue contractions.

4. The apparatus of claim 1, where the frequency of the first square wave signal is in an inclusive range of 1 Hz to 5,000 Hz.

5. The apparatus of claim 1, where the frequency of the second square wave signal is in an inclusive range of 1,000 Hz to 50,000 Hz.

6. The apparatus of claim 1, where the voltage increased mixed bi-polar square wave signal applied by the electrical contacts directly to a mammal's tissues creates standing electrical waves upon the polarity switching of the first square wave signal.

7. An apparatus for frequency stimulation of a mammal's tissues configured for applying micro-currents directly to skin of a mammal, the apparatus comprising:
   a power supply,
   a microcontroller,
   a quartz crystal for clocking said microcontroller, the quartz crystal having a fundamental frequency within 1% of a Fibonacci number in an inclusive range of 75,000 Hz to 102,000,000 Hz, a storage device storing one or more programs, said programs being timed sequences of Rife frequencies, and the storage device further storing instructions for controlling the microcontroller to perform steps comprising:

producing a first square wave signal having a frequency based at least in part upon a fundamental frequency of the quartz crystal and a Rife frequency in said one or more stored programs;

producing a second square wave signal having a frequency based at least in part upon a fundamental frequency of the quartz crystal with a variable duty cycle wherein the second square wave signal's frequency is at least four times greater than the first square wave signal's frequency;

alternating the variable duty cycle of the second square wave signal in step with the first square wave signal;

an H-bridge acting as an eXclusive OR (XOR) to modulate the first and second square wave signals to produce a mixed bi-polar square wave signal with a voltage based at least in part upon the power supply and the XOR modulation of the first and second square wave signals, a step-up transformer capacitively coupled to the H-bridge to increase the voltage of the mixed bi-polar square wave signal to overcome the skin resistance of a mammal's tissues, electrical contacts to apply the voltage increased mixed bi-polar square wave signal directly to a mammal's tissues, and wherein the variable duty cycle of the second square wave signal is varied such that the micro-currents of the voltage increased mixed bipolar square wave signal applied by the electrical contacts directly to a mammal's tissues have a current in an inclusive range of 0.1 milliamperes to 100 milliamperes being sufficiently low enough to not cause muscle tissue contractions.

8. The apparatus of claim 7, where the frequency of the first square wave signal is in an inclusive range of 1 Hz to 5,000 Hz.

9. The apparatus of claim 7, where the frequency of the second square wave signal is in an inclusive range of 1,000 Hz to 50,000 Hz.

10. The apparatus of claim 7, where the voltage increased mixed bi-polar square wave signal applied by the electrical contacts directly to a mammal's tissues creates standing electrical waves upon the polarity switching of the first square wave signal.

11. An apparatus for frequency stimulation of a mammal's tissues configured for applying micro-currents directly to skin of a mammal, the apparatus comprising:

a power supply, a microcontroller, a quartz crystal for clocking said microcontroller, the quartz crystal having a fundamental frequency within 1% of a Fibonacci number in an inclusive range of 75,000 Hz to 102,000,000 Hz, a storage device storing one or more programs, said programs being timed sequences of Rife frequencies, and the storage device further storing instructions for controlling the microcontroller to perform steps comprising:

producing a first square wave signal having a frequency based at least in part upon a fundamental frequency of the quartz crystal and a Rife frequency in said one or more stored programs;

producing a second square wave signal having a frequency based at least in part upon a fundamental frequency of the quartz crystal with a variable duty cycle wherein the second square wave signal's frequency is at least four times greater than the first square wave signal's frequency;

alternating the variable duty cycle of the second square wave signal in step with the first square wave signal;

an H-bridge acting as an eXclusive OR (XOR) to modulate the first and second square wave signals to produce a mixed bi-polar square wave signal with a voltage based at least in part upon the power supply and the XOR modulation of the first and second square wave signals;

a step-up transformer capacitively coupled to the H-bridge to increase the voltage of the mixed bi-polar square wave signal to overcome the skin resistance of a mammal's tissues, electrical contacts to apply the voltage increased mixed bi-polar square wave signal directly to a mammal's tissues, where the variable duty cycle of the second square wave signal is varied such that the micro-currents of the voltage increased mixed bipolar square wave signal applied by the electrical contacts directly to a mammal's tissues have a current in an inclusive current range of 0.1 milliamperes to 100 milliamperes being sufficiently low enough to not cause muscle tissue contractions, and where the frequency of the first square wave signal is in an inclusive range of 1 Hz to 5,000 Hz and the frequency of the second square wave signal is in an inclusive range of 1,000 Hz to 50,000 Hz, and where the voltage increased mixed bi-polar square wave signal applied by the electrical contacts directly to a mammal's tissues creates standing electrical waves upon the polarity switching of the first square wave signal.

* * * * *